United States Patent
Olson et al.

(10) Patent No.: US 8,852,156 B2
(45) Date of Patent: Oct. 7, 2014

(54) DEVICE FOR IMPLANTING MEDICAL CATHETERS

(75) Inventors: Kathryn Olson, San Diego, CA (US); Jayant Menon, San Diego, CA (US); Jonathan Dunbar, San Diego, CA (US)

(73) Assignee: Windrose Medical, LLC., San Diego, CA (US)

( * ) Notice: Subject to any disclaimer, the term of this patent is extended or adjusted under 35 U.S.C. 154(b) by 178 days.

(21) Appl. No.: 13/469,660

(22) Filed: May 11, 2012

(65) Prior Publication Data

US 2013/0204208 A1      Aug. 8, 2013

Related U.S. Application Data

(60) Provisional application No. 61/596,476, filed on Feb. 8, 2012.

(51) Int. Cl.
*A61M 5/178*      (2006.01)

(52) U.S. Cl.
USPC .................. 604/170.02; 604/167.06; 604/267

(58) Field of Classification Search
USPC .................. 604/167.06, 170.01, 170.02, 267; 27/24.1, 24.2
See application file for complete search history.

(56) References Cited

U.S. PATENT DOCUMENTS

| | | | |
|---|---|---|---|
| 918,437 A * | 4/1909 | Genung | 27/24.2 |
| 4,784,638 A | 11/1988 | Ghajar et al. | |
| 4,808,158 A * | 2/1989 | Kreuzer et al. | 604/500 |
| 4,950,232 A | 8/1990 | Ruzicka et al. | |
| 5,098,411 A | 3/1992 | Watson et al. | |
| 5,180,387 A | 1/1993 | Ghajar et al. | |
| 5,244,619 A | 9/1993 | Burnham | |
| 5,603,703 A | 2/1997 | Elsberry et al. | |
| 5,919,164 A * | 7/1999 | Andersen | 604/102.02 |
| 5,985,307 A * | 11/1999 | Hanson et al. | 424/423 |
| 6,193,691 B1 | 2/2001 | Beardsley | |
| 6,197,003 B1 | 3/2001 | Howard, III et al. | |
| 7,037,288 B2 | 5/2006 | Rosenberg et al. | |
| 7,174,222 B2 | 2/2007 | Tockman et al. | |
| 7,582,068 B2 | 9/2009 | Koullick et al. | |
| 7,972,308 B2 | 7/2011 | Putz | |
| 7,974,709 B2 | 7/2011 | Tockman et al. | |
| 8,029,473 B2 | 10/2011 | Carter et al. | |
| 8,083,736 B2 | 12/2011 | Mcclurken et al. | |
| 8,088,091 B2 | 1/2012 | Thomas et al. | |
| 2004/0064926 A1 * | 4/2004 | Adkins | 27/22.1 |
| 2007/0088295 A1 | 4/2007 | Bankiewicz | |
| 2007/0233007 A1 * | 10/2007 | Adams | 604/168.01 |
| 2008/0140008 A1 | 6/2008 | Keimel et al. | |
| 2010/0069855 A1 | 3/2010 | Ross | |
| 2010/0222732 A1 | 9/2010 | Sevrain | |
| 2012/0059285 A1 | 3/2012 | Soltani et al. | |
| 2012/0078159 A1 | 3/2012 | Wilson et al. | |

OTHER PUBLICATIONS

International Search Report and Written Opinion dated May 15, 2013 for PCT Application No. PCT/US2013/023696.

* cited by examiner

*Primary Examiner* — Emily Schmidt
(74) *Attorney, Agent, or Firm* — The Mueller Law Office, P.C.

(57) ABSTRACT

A stylet for use with a medical catheter has a lumen blocking portion and a shaft, where the shaft has a smaller effective diameter than the lumen blocking portion. The lumen blocking portion has an outer surface that is approximately flush with the catheter lumen in a working area of the catheter. The lumen blocking portion has a length capable of covering at least one side hole of the catheter.

27 Claims, 7 Drawing Sheets

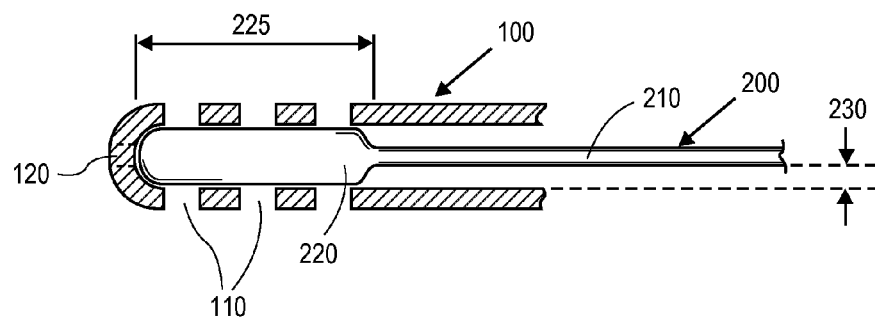
FIG. 3
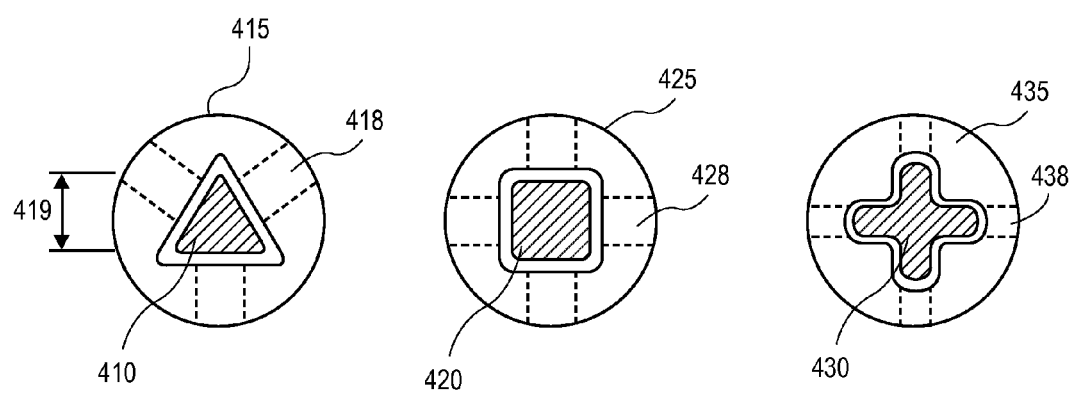
FIG. 4A  FIG. 4B  FIG. 4C

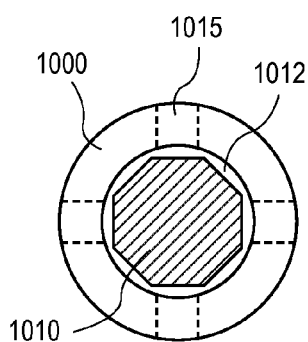 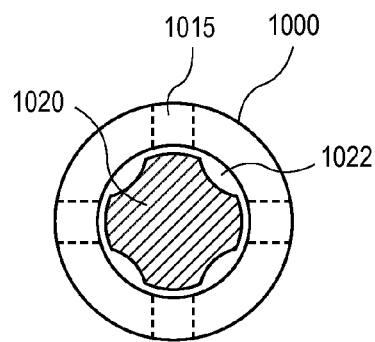 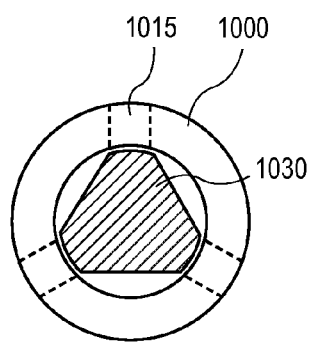
FIG. 10A   FIG. 10B   FIG. 10C
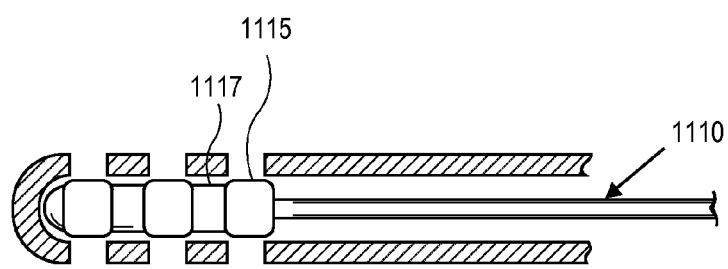
FIG. 11

DEVICE FOR IMPLANTING MEDICAL CATHETERS

RELATED APPLICATIONS

This application claims priority to U.S. Provisional Patent Application No. 61/596,476, entitled "Device for Implanting Medical Catheters," filed on Feb. 8, 2012, and hereby incorporated by reference for all purposes.

BACKGROUND OF THE INVENTION

Medical catheters are used to either remove fluid from or deliver fluid to a bodily organ. Catheters have holes on the end of a tube and/or along the sides. When catheters are inserted into the body, they can clog with soft tissue. When this occurs during a procedure and the catheter no longer allows fluid flow, the catheter is normally removed, cleaned, and re-inserted. Catheters can also become clogged after implantation due to a number of causes, including ingrowth of surrounding tissue.

One disease where catheter clogging post-surgery is a major cause of treatment failure is hydrocephalus. Hydrocephalus is a disease where the brain either produces too much cerebrospinal fluid (CSF) or is unable to reabsorb it in a normal manner, increasing the intracranial pressure (ICP) within the skull. Hydrocephalus can be a congenital disease where it affects 1 in every 500 children born or can be induced by a traumatic brain injury, tumor, or a number of other reasons. Normal Pressure Hydrocephalus (NPH) is a disease developed mainly in adults over the age of 65 where the pressure is within a normal range, but there is a slight excess of CSF that can lead to cognitive disabilities.

The most common treatment of hydrocephalus is to implant a shunt to divert the excess fluid from the brain to another part of the body. Shunts generally consist of a catheter implanted in the brain (ventricular catheter), a pressure or flow-regulating valve, and another catheter, which is most commonly implanted in the peritoneum. Fluid drains from the ventricle of the brain through the proximal (ventricular) catheter out of the skull and towards the valve, which ensures that the correct ICP is maintained. Cerebrospinal fluid then passes through the distal catheter to another area of the body, such as the peritoneum, where the excess CSF is reabsorbed by the body.

These shunts can fail due to a number of causes, but the most common causes of failure are obstruction and infection. 50% of shunts will fail within the first two years after implantation, and 85% of hydrocephalus patients undergo at least two shunt revision surgeries within their lifetime. It has been found that the main cause of shunt failure is catheter occlusion, with 30.4% of shunts failing due to occlusion of the proximal end—or ventricular catheter—and 13.7% failing due to occlusion of the distal end—or peritoneal catheter. This high incidence of failure, mainly due to obstruction, leads to the treatment of pediatric hydrocephalus costing the U.S. healthcare system more than $1B every year.

Long-term obstruction of the ventricular catheter is generally attributed to slow and progressive ingrowth of the choroid plexus, a vascular semi-mobile structure of the brain located inside the ventricle. Choroid plexus is found throughout the ventricular system and is typically just adjacent to ventricular catheters when they are placed.

Short-term obstruction occurs in the first few days after surgery, leading to costly and dangerous reoperation. This phenomenon of early clogging was thought to be the product of poor catheter placement. However, recent clinical trials using video-assisted placement have not decreased the rate of short- or long-term proximal catheter obstruction or improved clinical outcomes.

SUMMARY OF THE INVENTION

A stylet for use with a medical catheter has a lumen blocking portion and a shaft, where the shaft has a smaller effective diameter than the lumen blocking portion. The catheter has a lumen and a plurality of side holes in a working area of the catheter. The lumen blocking portion has an outer surface that is approximately flush with the catheter lumen in the working area of the catheter. The lumen blocking portion has a length capable of covering at least one side hole of the catheter.

BRIEF DESCRIPTION OF THE DRAWINGS

FIG. 3 depicts a cross-sectional view of an exemplary stylet of the present invention inserted into a catheter;

FIGS. 4A-4C illustrate embodiments of exemplary cross-sectional stylet and catheter shapes;

FIGS. 10A-10C are cross-sectional views of yet further embodiments of lumen blocking stylets;

FIG. 11 shows another embodiment of a lumen blocking stylet; and

DESCRIPTION OF THE EMBODIMENTS

A stylet device is disclosed which deters tissue from entering the fluid drainage or delivery holes of a catheter when the catheter is implanted in a body cavity. The stylet blocks the lumen of the catheter, particularly in the area where the fluid holes are located. The catheter may have holes in its side walls and/or may comprise an end hole. The device deters tissue from clogging the side holes, as well as tissue from entering the catheter by occupying the catheter lumen during implantation. After the catheter is implanted, the stylet is removed from the catheter lumen.

Figure 1:
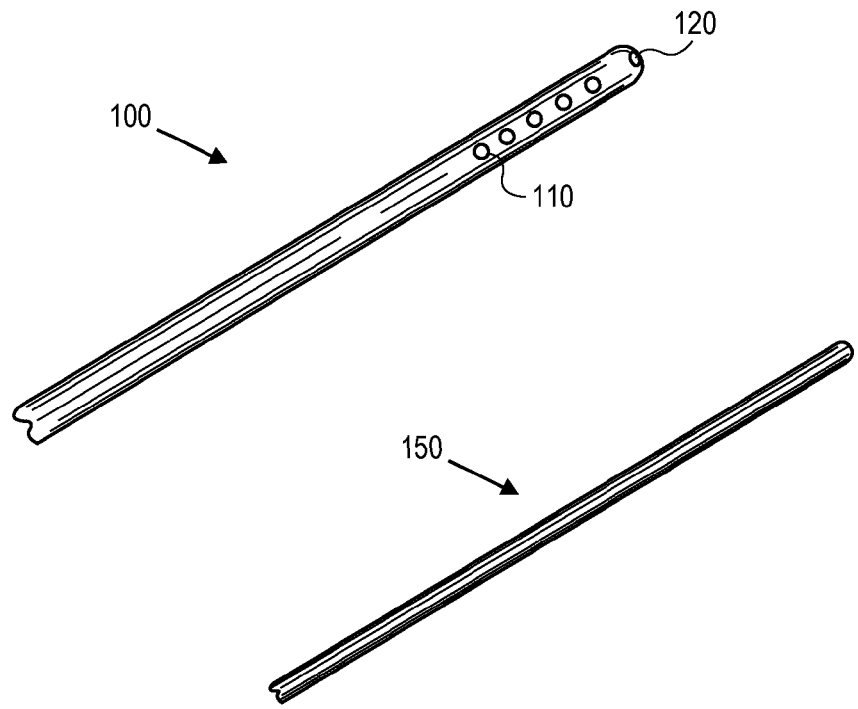
FIG. 1 is perspective view of a ventricular catheter and stylet known in the art.

FIG. 1 illustrates a typical ventricular or drainage catheter 100. Catheter 100 has side holes 110, and may also include an end hole 120 at its proximal tip. Note that for the purposes of this disclosure, "proximal" shall refer to the direction toward the tip of a device; that is, most proximal to the site—such as the brain—that is to be treated. "Distal" shall refer to the direction toward the end held by the user; that is, the end that is most distal from the area to be treated. During a procedure to implant ventricular catheters, neurosurgeons conventionally implant the catheter 100 with the aid of a simple metal stylet 150 which has a uniform diameter along its entire length. The stylet 150 is placed inside the catheter 100 during implantation, CSF is observed, and the stylet is removed prior to connecting the ventricular catheter 100 to a flow-regulating valve. During surgery, it sometimes can occur that the catheter 100 is implanted and the stylet 150 removed, but no CSF fluid flow is observed because the catheter 100 has become clogged with brain tissue. Tissue enters the catheter 100 through the holes 110 along the sides, and end hole 120 if present, as it is inserted into the brain. The holes 110 in the catheter wall cause a cheese-grating type of effect on the brain tissue. Research using lamb brains and gelatin-based brain tissue substitutes shows the effect of pressure in the brain tissue increases the incidence and magnitude of catheter clogging by this cheese-grating phenomenon.

During typical surgery, the catheter is assumed to be clogged and is immediately removed, cleaned, and replaced if no fluid is seen exiting the catheter after being placed in the ventricle. However, if the catheter is placed inside the ventricle and some CSF is seen exiting the catheter, it is assumed to be clear of obstruction and the surgeon continues with the operation, connecting the ventricular catheter to a flow-regulating valve and then the distal catheter. In vitro testing with lamb brains in association with this disclosure has shown that even when there is fluid flow observed at the distal end of the catheter, there can be partial obstruction by brain tissue at the tip area of the catheter. Therefore, even if fluid is exiting the catheter, the catheter may be critically obstructed with tissue.

This incidence of clogging is also seen when ventricular catheters are implanted in patients as external ventricular drains, where the fluid in the ventricles is drained from the brain to a receptacle outside of the body. External ventricular drains are important for acute conditions of brain injury, including swelling, hemorrhaging or acute hydrocephalus.

Physicians have experienced clogging during catheter implantation, which is an annoyance during surgery, but is generally dealt with immediately by removing the catheter, cleaning it, and then replacing it. However, studies are not conclusive whether the passage of the catheter through the brain has an effect on catheter clogging post surgery. Observations during in vitro tests related to this disclosure reveal that passing a catheter through tissue under pressure causes significant portions of tissue to enter the catheter. During these tests, it was seen that the catheter may still allow fluid to flow through, despite minor obstructions due to tissue. Any fluid flow is sufficient for the physician to continue with surgery not knowing that the catheter may be partially obstructed, as the surgeon cannot see the tip of the catheter located within the ventricle. However, it is likely that a partially obstructed catheter during surgery has a higher likelihood of complete clogging post-surgery. This may account for the high incidence of catheter clogging within the first month after shunt implantation surgery in patients with hydrocephalus. Clogging can be observed even within the first few days after surgery, which is not likely to be caused by choroid plexus tissue ingrowth. When catheters clog post-surgery, the patient must undergo another surgery, where the ventricular catheter is replaced with a new one.

Although few people are concerned with catheters clogging when they are passed through the brain, there are a number of people concerned with causing damage to the brain during catheter implantation. Accordingly, some devices known in the art have been invented with the intention of minimizing this "damage to the brain." For instance, side holes in ventricular catheters have been designed to be angled, placed in helical patterns along the catheter, or recessed within grooves. Other products have utilized porous membranes, anti-occlusion agents, or radioactive inserts in catheters to deter tissue growth after implantation. For catheters with end holes, stylets have been designed to protrude through the end hole, or to have an enlarged tip blocking the external surface of the end hole, to inhibit tissue from entering the catheter during placement. Stylets and guidewires in the art which do not have a uniform diameter along their entire length are tapered toward their tip, to reduce trauma and improve navigability.

The present invention provides features to reduce tissue accumulation in the fluid drainage holes of a catheter, and the catheter lumen itself, by blocking the catheter holes from the interior of the catheter. In one embodiment, a stylet with a larger diameter along a defined length at the working end of the stylet is provided, to deter tissue from entering the catheter lumen. The size and shape of the stylet is designed to be approximately equal to the inside of the catheter in the region of the fluid conduit holes, thereby blocking the catheter lumen when it is passed through the brain or other soft tissue. The shaft of the stylet is smaller than the portion of the stylet that blocks the catheter lumen. The stylet is then removed through the lumen of the catheter after the catheter is implanted, leaving the lumen and holes exposed to allow fluid to pass through. Additionally, embodiments of the present invention may have optional features such as a fluid conduit for the purposes of viewing fluid flashback during implantation and to prevent an undesirable suction effect. In other embodiments, the length of the lumen blocking portion may be designed to allow fluid flashback from one or more of the catheter side holes.

Figure 2:
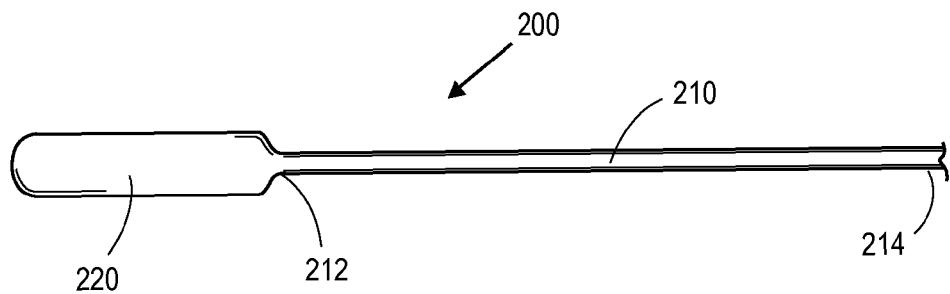
FIG. 2 is a side view of a lumen blocking stylet in one embodiment of the present invention.

FIG. 2 illustrates one embodiment of the present invention, in which a stylet 200 has a shaft 210 and a larger diameter lumen blocking portion 220. The shaft 210 has a proximal end 212 and a distal end 214, with the lumen blocking portion 220 being located at the proximal end 212 of shaft 210. Stylet 200 may be a metal rod, such as stainless steel or titanium, or other metal alloy or it may be a hard polymer, composite material, or other biocompatible material. Furthermore, stylet 200 may have surface coatings or treatments to reduce friction or inhibit tissue adherence, such as treatments to modify surface topography or composition. The surface of the stylet may also be passivated via citric acid or other means to prevent corrosion on the stylet surface.

FIG. 3 shows a lengthwise cross-sectional view of a working area—that is, where the side holes are located—of the catheter 100, with stylet 200 inserted. In FIG. 3, the outer surface of lumen blocking portion 220 is substantially flush with the inner surface of catheter 100. That is, the lumen blocking portion 220 is sized to approximately match the inner lumen of the catheter, which beneficially inhibits tissue accumulation in the catheter lumen during implantation. For example, the lumen blocking portion 220 may have a circular cross-section with a diameter of 90%-99% of the catheter diameter lumen, or in some embodiments 95%-99% of the catheter diameter lumen. For example, in some embodiments the diameter of the lumen blocking portion of the stylet may be 0.000 to 0.010" less than the catheter lumen, in further embodiments, such as for tissue having properties similar to the brain, the diameter of the lumen blocking portion of the stylet may be 0.000-0.008" or 0.001-0.005" or 0.002-0.004" less than the catheter lumen diameter. For tissue in other areas of the body, the difference in diameters between the lumen blocking portion of the stylet and catheter lumen may have different values to address the specific tissue properties in that area. Research has found that when the lumen blocking portion is less than on the order of 90%-95% of the catheter lumen, it is ineffective at preventing tissue from blocking the holes of the catheter. In this embodiment of FIG. 3, the lumen blocking portion 220 has a length 225 that covers all of the side holes 110. During testing, it has been shown that fewer of the holes of the catheter become filled with tissue when the lumen-blocking stylet, such as stylet 200, is present to reduce the likelihood of tissue from entering the catheter lumen. Although straight stylets have been used in the art, tissue accumulation in the holes of the catheter during insertion has only recently been identified to be a potential cause of catheter obstruction and failure. Previously, obstruction has been attributed entirely to tissue growing into the catheter after the catheter has been implanted for some time. Research has found that not only does tissue enter the holes of the catheter during implantation, but it often enters the catheter lumen as well. The lumen blocking stylet also reduces the number of clogged holes because the tissue is more loosely attached to the catheter. With the multi-diameter stylets, the tissue in the catheter side holes either does not attach at all, or falls off more easily. This is mainly because there is no tissue in the lumen of the catheter connecting the tissue between the holes and anchoring it to the catheter.

Note in the embodiment of FIG. 3, the stylet 200 also deters tissue from entering the optional end hole 120 in that the tip of the lumen blocking portion 220 blocks the end hole from the interior of the catheter lumen. The proximal tip of lumen blocking portion 220 is sized to be larger than end hole 120 so that it does not protrude through end hole 120, but instead remains within catheter 100. In other embodiments, the tip of stylet 200 may protrude through the end hole 120.

Still referring to FIG. 3, shaft 210 has a smaller diameter than the lumen blocking portion 220, which advantageously reduces the friction for removing the stylet 200 from a catheter, as well as reinserting the stylet, if necessary. If the stylet 200 were to be configured along its entire length with the diameter of the lumen blocking portion 220, the stylet 200 would be too difficult to remove from the catheter 100. Additionally, a stylet with a large diameter throughout would be too heavy for surgeons to use, in that gravity may change the trajectory of catheter implantation. In addition, it is important for the surgeon to be able to feel when the catheter has entered the ventricle of the brain, or other tissue in which a catheter is being used, in order to properly implant or place the catheter in the open area of the body requiring fluid drainage. Stylets that are thick along the entire stylet length do not provide the surgeon with the same feel and may prevent proper catheter placement. If the stylet were to be one diameter along its full length, but sized smaller to facilitate removal from the catheter as in conventional straight stylets, the size of the stylet would not sufficiently prevent tissue from entering the catheter's side holes. Thus in this embodiment, the thinner portion of the stylet—shaft 210—provides less friction within the catheter 100, gives the surgeon the same feel during surgery and facilitates easy removal of the stylet 200, despite the larger diameter of the lumen blocking portion 220.

The lumen blocking portion 220 is carefully sized to deter tissue from entering the side holes of the catheter, while the smaller shaft size allows for the stylet to be easily inserted and removed by the user. The diameter of the lumen blocking portion of the stylet may be, for example, 95-99% of the catheter lumen diameter. For instance, for a catheter lumen of approximately 0.0540" diameter, the stylet diameter may have a diameter of 0.0510-0.0535" in the lumen blocking region. To provide another example, for a catheter lumen of approximately 0.0748" diameter, the stylet may have a diameter of 0.0710-0.0745" in the lumen blocking region. Research has found that when the lumen blocking portion is 90% of the catheter lumen or less, it is ineffective at preventing tissue from blocking the holes of the catheter.

The shaft may be significantly less than 95% of the diameter of the lumen blocking portion of the stylet in order to minimize the weight of the device and maintain the tactile feedback during surgery, but the shaft must still be thick enough to provide structural rigidity during catheter implantation. In some embodiments, the shaft diameter may be, for example, up to 95% of the diameter of the lumen blocking portion. For example, a shaft diameter may be 0.030 to 0.095" for lumen blocking diameters of 0.050 to 0.100" for stylets used in brain tissue or tissue of similar penetrability. For applications in other parts of the body, the shaft may require a larger or smaller diameter according to the tissue properties of that region. For example, a denser tissue may require a larger shaft diameter to accommodate higher forces to push the stylet through the tissue, while a softer tissue may require a smaller diameter for more sensitivity when advancing the stylet.

Note also in the stylet 200 of the embodiment of FIGS. 2 and 3 that the outer surface of shaft 210 is non-collinear with the outer surface of lumen blocking portion 220. In other words, the shaft 210 is offset by a distance 230 (FIG. 3) from a line extending from the perimeter of lumen blocking portion 220. While the shaft 210 need not necessarily be coaxial or centered with lumen blocking portion 220, having shaft 210 inset from contacting the catheter walls reduces friction due to the shaft 210. In other embodiments, not shown, the outer surface of the shaft 210 may be aligned—that is, collinear—with the outer surface of the lumen blocking portion 220 such that the distance 230 is zero.

While typically a catheter lumen will be circular in cross-section, the stylet may be adapted for catheters of other cross-sectional shapes. FIGS. 4A-4C show cross-sectional views of exemplary stylets 410, 420 and 430 having various shapes, to block lumens of corresponding catheters. In FIG. 4A, stylet 410 has an outer surface that is substantially flush with the triangular lumen of catheter 415. For example, the stylet size may be designed to have 0.000 to 0.005" of clearance between the stylet 410 and the lumen of catheter 415. The surfaces of stylet 410 block side holes 418 of catheter 415. Similarly, in FIG. 4B a stylet 420 and catheter 425 have matching square-shaped cross-sections, and the surfaces of stylet 425 are adjacent to side holes 428. In FIG. 4C a stylet 430 and catheter 435 have a curvilinear cross shape, in which the ends of the arms block side holes 438. Other polygonal or curvilinear shapes are possible. In the case of these non-circular cross-sections of FIGS. 4A-4C, the lumen blocking portion has a size defined by an effective diameter, which is the largest distance across the shape. For example, the effective diameter of the triangular stylet 410 would be the height 419 of the triangle. For a circular cross-section, the effective diameter is the same as the diameter of the circle. In some embodiments, the shafts of these irregularly shaped stylets may have the same cross-sectional shape as the lumen blocking portion. In other embodiments the shaft may have a different shape, such as a standard circular rod.

Figure 5A:
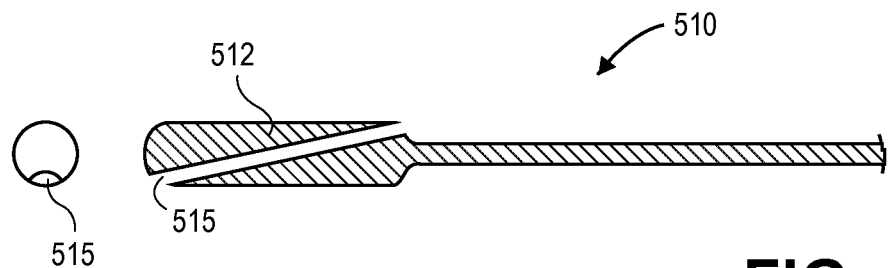
FIGS. 5A-5E are area and lengthwise cross-sectional views of embodiments of stylets which enable fluid flashback.
Figure 5B:
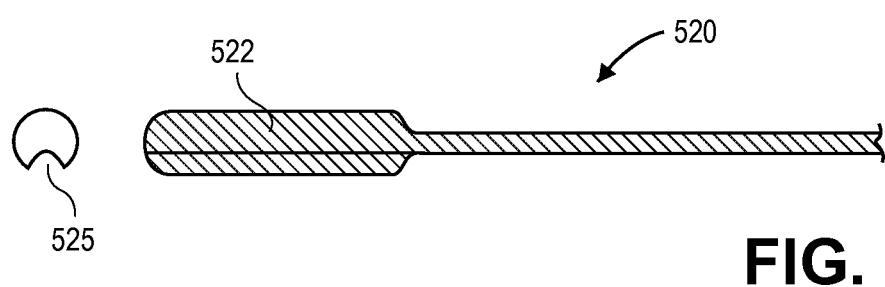
Figure 5C:
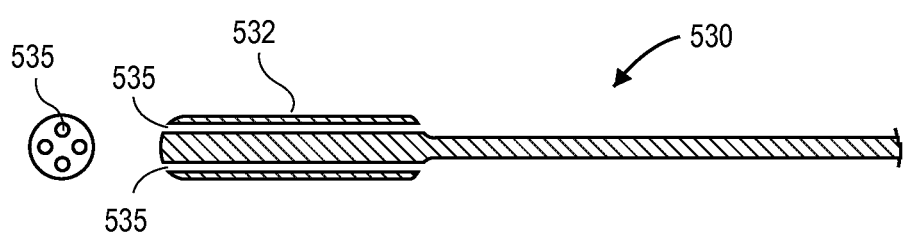
Figure 5D:
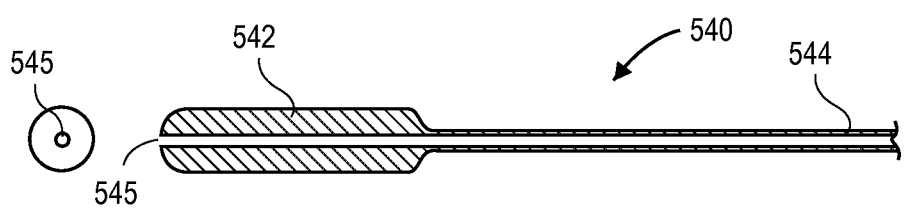
Figure 5E:
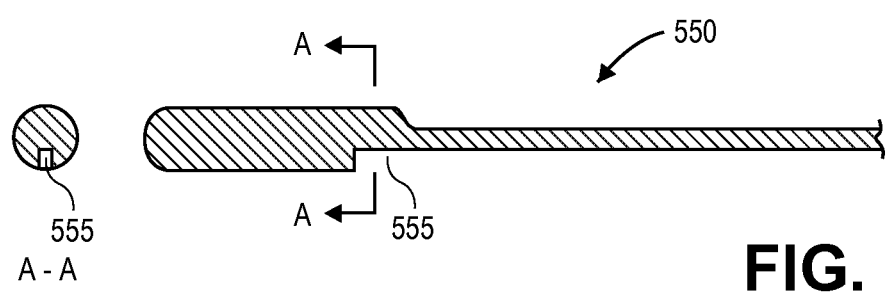

Stylets enable surgeons to implant catheters into an area requiring fluid drainage, and surgeons are able to observe fluid flow through the catheter, even around the existing stylet, once they have reached the desired site. This fluid flow, known as flashback, indicates to them that they have reached the proper area of the body for fluid drainage. This is especially common when the excess fluid increases the fluid pressure in that area of the body, as in hydrocephalus treatment or pleural effusion. FIGS. 5A-5E illustrate end views and cross-sectional lengthwise views (taken along the longitudinal axis of the stylet) of exemplary embodiments of stylets which enable fluid flashback. In FIG. 5A, stylet 510 has a transverse channel 515 through its lumen blocking portion 512 to allow fluid to flow from the proximal (tip) end of the lumen blocking portion 512 to the distal (shaft) end. Stylet 520 of FIG. 5B has a C-shaped groove 525 along the exterior surface of lumen blocking portion 522 to serve as a fluid passageway. Stylet 530 of FIG. 5C has cylindrical channels 535 extending straight through the interior of lumen blocking portion 532. In FIG. 5D, stylet 540 has a channel 545 extending through both the lumen-blocking portion 542 and the shaft 544. In FIG. 5E, stylet 550 has a square notch 555 at the distal end of lumen blocking portion 552, as seen in more detail in cross-section A-A. This notch 555 allows fluid to flow from the most distal side hole of a catheter. Note that the fluid conduits shown in FIGS. 5A-5E may be configured with shapes other than those depicted, such as rectangular, oval-shaped, or curvilinear. Furthermore, the number of channels may vary from one or more. The channels of FIGS. 5A-5D provide a fluid path extending through the length of the lumen blocking portion, so that fluid may flow from the catheter holes to the other end of the ventricular catheter. The notch of FIG. 5E also allows fluid flashback, from one or more side holes. These embodiments may be manufactured using standard machining practices such as drilling, laser cutting, etching, computer numerical control (CNC) machines, and the like. The stylets may be made of a biocompatible metal or hard polymer, for example, medical grade stainless steel.

Figure 6A:
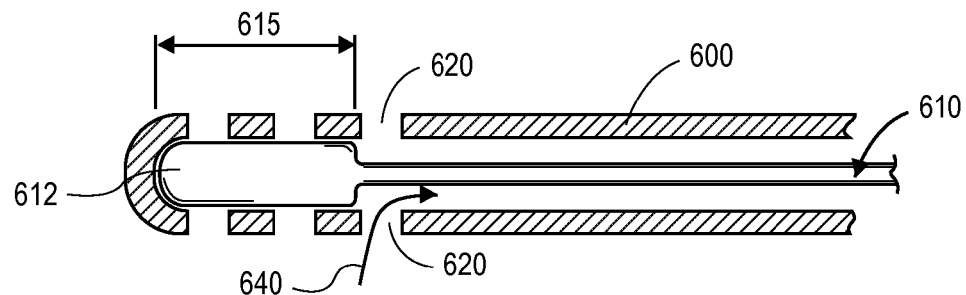
FIGS. 6A-6B show cross-sectional views of further embodiments of stylets which enable fluid flashback.
Figure 6B:
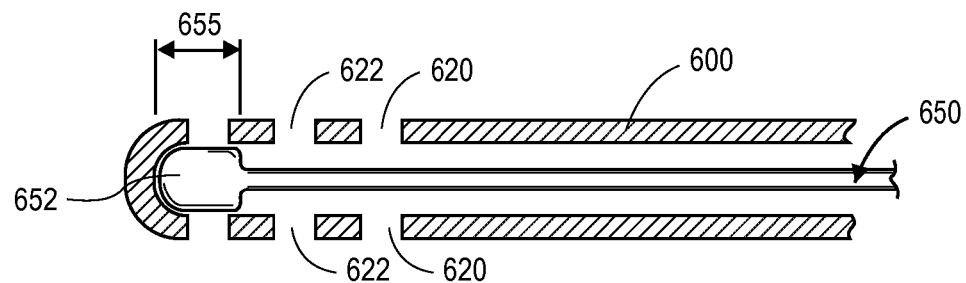

FIGS. 6A-B depict further embodiments of stylets which enable fluid flashback. In FIG. 6A, a stylet 610 has a lumen blocking portion 612 with length 615 that is shorter than the working area of the catheter, so that the most distal holes 620 remain exposed when the stylet 610 is fully inserted into the catheter 600. Thus, when the ventricular catheter 600 is properly placed in the ventricle, with stylet 610 inside, fluid may flow through distal holes 620 as indicated by arrow 640. This design of FIG. 6A may be easier to manufacture than a hollow stylet, such as in FIG. 5D. When the stylet 610 is removed from the catheter 600 after the catheter has been placed, any minimal tissue that may have entered the catheter 600 through the distal holes 620 will be removed by stylet 610. That is, the stylet 610 in effect reams the inner lumen of catheter 600 when the stylet 610 is withdrawn.

In FIG. 6B, stylet 650 has an even shorter length 655 for lumen blocking portion 652 than stylet 610. This shorter design of FIG. 6B reduces removal/insertion friction between the stylet 650 and catheter 600 even further, reduces the amount of material required for stylet 650, and takes advantage of the reaming ability of the stylet 650 to remove any tissue that may enter exposed side holes 620 and 622. In other embodiments, stylets may have lumen blocking portions with a length that cover any number of side holes, ranging from one side hole to all of the side holes on the catheter. In yet further embodiments, not shown, the stylet may be used for reaming purposes only. In such embodiments, the lumen blocking portion has a diameter sized with respect to the catheter lumen as described above, which provides a size large enough to be able to clear tissue from the catheter lumen, but has a length which does not necessarily need to cover the sides holes in the catheter.

The stylets of FIG. 5E and FIG. 6A present further benefits regarding fluid flashback. When using conventional stylets for catheter placement, it may occur that the surgeon accidentally inserts the catheter such that some of the holes are located in the ventricle, or other area of the body requiring fluid drainage, while the other more distal holes are improperly located in the brain or other tissue. Once implanted in this way, brain tissue could easily grow into the catheter's most distal holes and even the catheter lumen, causing the catheter holes and/or lumen to be obstructed and not allow fluid drainage or delivery. In the embodiments illustrated in FIGS. 5E and 6A, the stylets are configured to enable only the most distal holes to be open to allow fluid flashback, while the proximal catheter holes are advantageously blocked by the stylet to prevent tissue from entering the catheter. These configurations would ensure that the entire working length of the catheter—the length in which the side holes are located—is properly inserted within the ventricle before the surgeon is able to view fluid flashback, which is an indicator of proper catheter placement. This will maximize the number of open holes for fluid flow by preventing tissue accumulation, while improving the ability to ensure proper placement compared to conventional stylets, and thereby preventing tissue from growing into the catheter due to catheter misplacement and blockage of the most distal holes.

Figure 7A:
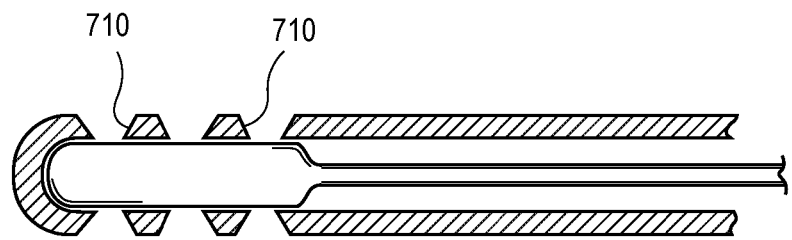
FIGS. 7A-7B illustrate cross-sectional views of other embodiments of catheter holes.
Figure 7B:
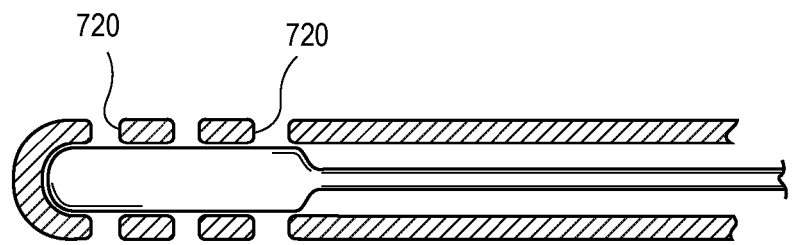

In other embodiments of the invention, the ventricular catheter itself may incorporate features to reduce tissue intrusion into the side holes and/or the catheter lumen. For example, the catheter holes may be modified to reduce tissue adherence to the holes when the stylet is passed through the brain. For example, in FIG. 7A the catheter holes may have beveled edges 710. Alternatively, the catheter holes may have rounded/filleted edges 720 as in FIG. 7B. These edges 710 and 720 may be less traumatic to tissue during entry, and thus reduce tearing of tissue during implantation. These hole modifications may also reduce tissue adherence to the edges of the hole, causing tissue to fall off during stylet removal. Combining these catheter hole modifications of FIGS. 7A-B with the utilization of the lumen blocking stylet would provide a comprehensive solution for implanting medical catheters, deterring tissue from filling either the catheter holes or the catheter lumen.

Figure 8:
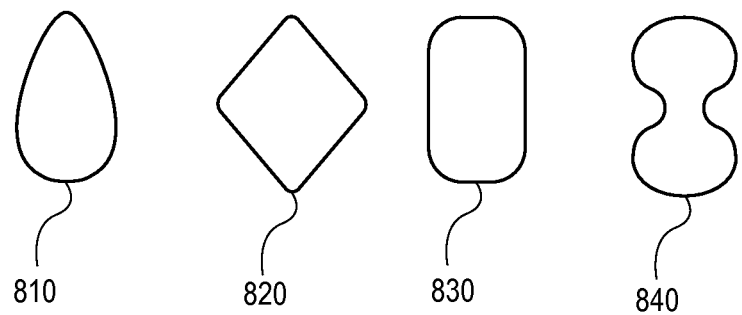
FIG. 8 depicts embodiments of alternative shapes for catheter holes.

FIG. 8 illustrates other embodiments of catheter modifications, in which the shapes of the holes may be non-circular. Experimental testing has found that the removal of a stylet with a thicker lumen blocking portion can drag tissue with it as it is being pulled out of the catheter, moving the tissue across the opening of a side hole. This dragging effect leaves the hole partially open at its lateral edge closer to the catheter tip, and pushes the tissue toward the opposite side of the hole (distal edge), leaving the hole largely unobstructed. The hole designs of FIG. 8 aim to capture the tissue at the distal portion of the hole when the stylet is removed and to allow an elongated, larger open hole area at the proximal portion of the hole. Hole 810 is a teardrop-type shape where the tissue may be captured at the top of the hole, leaving the large bottom hole portion open. Hole 820 is a diamond shape providing tissue capture at the top of the hole, hole 830 an oval providing an elongated hole area to allow more open hole space at the bottom of the hole, and hole 840 a figure-eight curvilinear shape to allow tissue capture at the top of the hole and significant open hole space at the bottom of the hole area. Other variations of these shapes may be possible without departing from the scope of this invention.

Figure 9A:
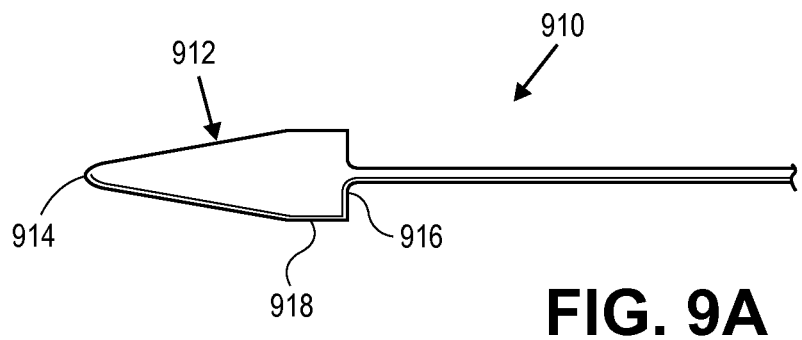
FIGS. 9A-9B depict side views further embodiments of stylets of the present invention.
Figure 9B:
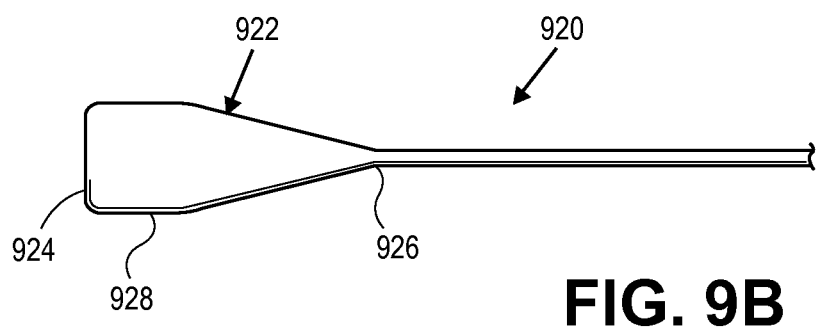

While the above embodiments depict the lumen blocking portion as having a single diameter, in some embodiments the lumen blocking portion may vary in diameter along its length. FIG. 9A depicts an exemplary stylet 910 with a lumen blocking portion 912 that has a smaller diameter at its proximal end 914 than at its distal end 916. Note that the dimensions shown are exaggerated for clarity. The lumen blocking portion 912 may have a flat portion 918 to facilitate hole-blocking of a catheter. In the embodiment of FIG. 9B, stylet 920 has a lumen blocking portion 922 that has a larger diameter at its proximal end 924 than its distal end 926. A flat portion 928 may be incorporated to block side holes of a catheter. The lumen blocking portions 912 and 922 of FIGS. 9A and 9B may be designed to block some or all of the side holes of a catheter, by varying the length of flat portions 918 and 928.

In further embodiments, the stylets may contact the catheter lumen at only certain sections around its perimeter. For example, in FIG. 10A stylet 1010 may have an octagonal cross-section, such that alternating surfaces are positioned to cover holes 1015 that are spaced every 90 degrees around the circumference of the catheter 1000. By having the stylet 1010 contact only certain portions of the inner lumen of catheter 1000, friction is reduced. Furthermore, gaps 1012 between the stylet 1010 and catheter 1000 may be used for fluid flow. In the embodiment of FIG. 10B, stylet 1020 has four concave grooves, creating even larger gaps 1022 than gaps 1012 to serve as fluid conduits between catheter 1000 and stylet 1020. FIG. 10C illustrates an embodiment where the catheter 1000 has holes 1015 spaced 120 degrees apart, with a corresponding stylet 1030 of triangular cross-section. Stylet 1030 has flattened edges at the vertices of its triangular shape, where the side holes 1015 are to be covered.

FIG. 11 illustrates yet another embodiment in which a stylet 1110 has a lumen blocking portion with intermittent raised portions 1115 and recessed portions 1117. Such a design may reduce friction compared to a lumen blocking portion of a single diameter, such as in FIG. 2, while still enabling multiple side holes to be covered. The effective diameter of the lumen blocking portion is the diameter of raised portions 1115. By reducing friction, this design may enable the stylet to have a larger effective diameter of the lumen blocking portion, which can be important to preventing tissue accumulation in the holes.

In yet further embodiments, not shown, stylets may have lumen blocking portions designed to accommodate other catheter hole configurations. For example, a catheter may have holes of varying size, such as multiple holes which are progressively smaller or larger along the catheter length, or holes positioned in a helical pattern. Corresponding stylets may have lumen blocking portions designed to cover these specific hole locations and sizes.

Figure 12A:
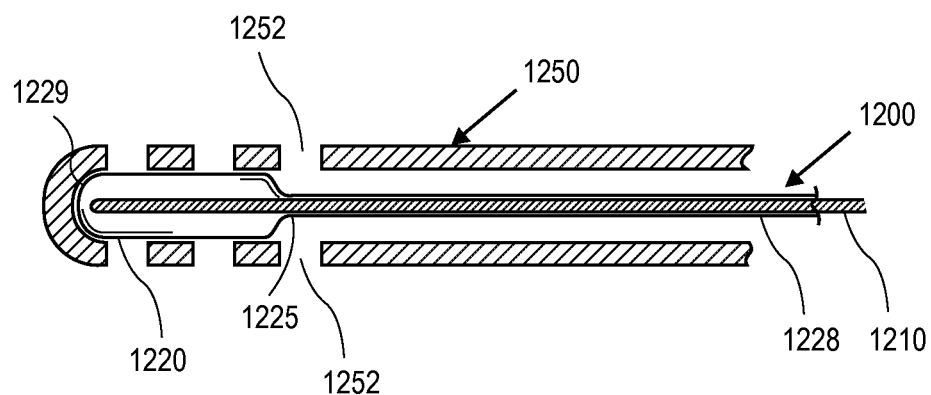
FIGS. 12A and 12B illustrate cross-sectional views of an alternative embodiment of a lumen blocking stylet.
Figure 12B:
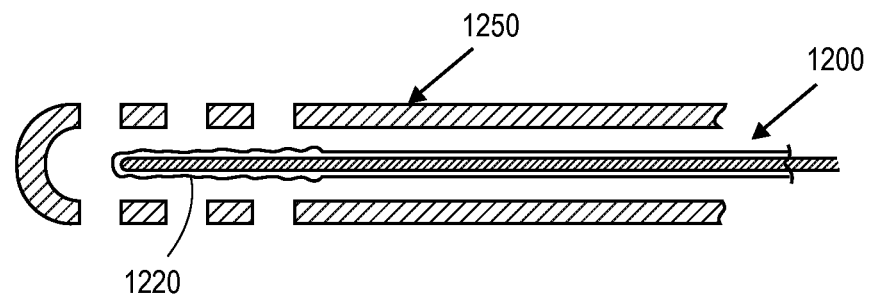

FIGS. 12A and 12B show an alternative embodiment of a lumen blocking stylet 1200, having a shaft 1210 and an inflatable lumen blocking portion 1220. In FIG. 12A, the lumen blocking portion 1220 is shown in an inflated state, in which the diameter of the lumen blocking portion 1220 is approximately flush with the lumen of catheter 1250. This inflated state of FIG. 12A would be used during insertion of catheter 1250 into the target region of the body. The length of the lumen blocking portion 1220 is designed such that its distal end 1225 allows distal holes 1252 of catheter 1250 to remain exposed for fluid flashback. The lumen blocking portion 1220 may be a balloon fabricated from, for example, polyethylene, polyethelene terephthalate, nylon, polyurethane, silicone, polyamides, polyether block amides (e.g., PEBAX®), or other balloon materials known in the art. In some embodiments, the balloon material is non-compliant. The lumen blocking portion 1220 is inflated via inflation lumen 1228 of stylet 1200. The stylet 1200 may be inflated using, for example, saline or contrast agents. Shaft 1210 may be fabricated from a biocompatible metal or a hard polymer, such as a medical grade stainless steel. Note that although shaft 1210 is depicted as extending to tip 1229 of stylet 1200, in other embodiments the shaft 1210 may terminate at distal end 1225 of lumen blocking portion 1220. In other embodiments, the shaft 1210 may terminate anywhere between distal end 1225 and tip 1229 of stylet 1200. FIG. 12B shows the stylet 1200 with the lumen blocking portion 1220 deflated, for removal of stylet 1200 from catheter 1250. This deflated configuration of FIG. 12B may decrease friction within catheter 1250 and thus facilitate removal of the stylet 1200.

In methods of use for the stylets, the stylet is first inserted into the catheter, or may come packaged as pre-inserted into the catheter. The catheter with stylet is then passed into the brain such that the tip rests within the ventricle or other body cavity. The holes in the catheter are thereby blocked by the lumen blocking portion of the stylet device that is located inside the catheter during catheter implantation. In embodiments where the option for fluid flashback is present, the physician may watch for flashback to occur, to indicate proper placement of the catheter. After placement is verified, the modified stylet is then removed through the lumen of the catheter, leaving the catheter holes exposed to allow fluid to pass through.

The stylets, which feature a lumen blocking portion to fill the working area of a catheter and a shaft of a smaller effective diameter than the lumen blocking portion, beneficially deter tissue from entering the side holes of a catheter and the catheter lumen. The smaller shaft size enables easy insertion and removal of the stylet, and allows for the necessary tactile feedback to the surgeon to aid in catheter placement. Fluid flashback is also optionally provided for by various fluid conduit configurations and varying lengths of the lumen blocking portion, and in configurations that may help to improve complete catheter placement within a body cavity. The stylets advantageously do not change existing neurosurgical procedures, can easily be removed and replaced, can be modified to accommodate catheters of varying diameters as well as different sized or shaped holes, and do not require any modifications to existing catheters to produce the desired results.

The embodiments of the invention can also be used to implant medical catheters into other parts of the body, including, but not limited to: the brain or other parts of the central nervous system (CNS), kidneys, peritoneal cavity, thorax, chest, abdomen, pelvis, liver, vasculature, eye, trachea, lung, ear, uterus, pleural cavity, peritoneum, ventricles or atria of the heart, blood vessels, and the like, in order to drain fluid or deliver a therapeutic. These catheters may be used for fluid drainage, including but not limited to: dialysis, peritoneal dialysis, lumbar shunting, pleural effusion, ascites, post operative drainage, angiography, wound drainage, lymphatic drainage, urinary drainage, biliary drainage, pneumothorax, hematomas, bilomas, urinomas, cysts, abscesses, pseudocysts, portasystemic shunting, TIPS, portacaval shunting, peritovenous shunting, thorontocentisis, paracentesis, pericardiocentesis, pericardial effusions, chest drainage, gastrointestinal feeding tubes, and the like. The apparatus and methods of the invention may also be used for fluid or tissue infusion, such as imaging (for example, contrast agents), or delivering therapeutics intravenously or otherwise and the treatment of any other disease requiring catheter placement, particularly catheters with holes along the sides. For example, embodiments of the invention may be used for in vitro fertilization, insulin delivery for diabetics, pain medication delivery, chemotherapy delivery, as well as delivery of drugs to treat Alzheimer's disease, spasticity, Parkinson's disease and others. Furthermore, the devices of the present invention are relevant in any application in which a catheter must pass through soft tissue that could enter holes along the sides of a catheter.

While the specification has been described in detail with respect to specific embodiments of the invention, it will be appreciated that those skilled in the art, upon attaining an understanding of the foregoing, may readily conceive of alterations to, variations of, and equivalents to these embodiments.

These and other modifications and variations to the present invention may be practiced by those of ordinary skill in the art, without departing from the spirit and scope of the present invention. Furthermore, those of ordinary skill in the art will appreciate that the foregoing description is by way of example only, and is not intended to limit the invention. Thus, it is intended that the present subject matter covers such modifications and variations.

What is claimed is:

1. A stylet capable of being inserted into a catheter, the catheter having a catheter lumen, a tip, and a plurality of side holes, wherein the side holes are located in a working area of the catheter, the stylet comprising:
a shaft having a proximal end and a distal end; and
a lumen blocking portion at the proximal end of the shaft, wherein the lumen blocking portion has an outer surface approximately flush with the catheter lumen in the working area of the catheter, wherein the outer surface of the lumen blocking portion has a first effective stylet diameter that is 90-99% of the catheter lumen diameter, wherein the lumen blocking portion has a length capable of covering at least one side hole in the plurality of side holes when the catheter is inserted through a specified volume of tissue, and wherein the covering of at least one side hole is capable of reducing tissue accumulation in a side hole in the plurality of side holes when the catheter is inserted through the specified volume of tissue;
wherein the shaft has a second effective stylet diameter distal to the lumen blocking portion, and wherein the second effective stylet diameter is less than the first effective stylet diameter, and wherein the shaft has a rigidity which enables the catheter to penetrate the specified volume of tissue;
wherein the tissue is live tissue chosen from the group consisting of the brain, central nervous system, fat, muscle, connective tissue, lung, liver, pancreas, uterus, trachea, esophagus, stomach, intestines, colon, pleura, chest wall, and kidneys.

2. The stylet of claim 1, wherein the lumen blocking portion has a circular cross-section, and wherein the first effective stylet diameter is the diameter of the circular cross-section.

3. The stylet of claim 1 further comprising a stylet fluid path extending through the length of the lumen blocking portion.

4. The stylet of claim 3 wherein the stylet fluid path comprises a passageway in an interior of the lumen blocking portion.

5. The stylet of claim 3 wherein the stylet fluid path comprises a passageway on an exterior surface of the lumen blocking portion.

6. The stylet of claim 3 wherein the stylet fluid path further comprises a stylet lumen extending through the shaft of the stylet.

7. The stylet of claim 1 wherein the length of the lumen blocking portion is capable of covering the entire plurality of side holes when the stylet is fully inserted to the tip of the catheter.

8. The stylet of claim 1 wherein the length of the lumen blocking portion allows at least a portion of one side hole to remain exposed when the stylet is fully inserted to the tip of the catheter.

9. The stylet of claim 1 wherein the second stylet diameter is less than 95% of the first stylet diameter.

10. The stylet of claim 1 wherein an outer surface of the shaft is non-collinear with an outer surface of the lumen blocking portion.

11. The stylet of claim 1 wherein the catheter has an end hole at the tip of the catheter, and wherein the lumen blocking portion of the stylet is configured to prevent protrusion of the stylet through the end hole.

12. The stylet of claim 1 wherein the lumen blocking portion is fabricated from a biocompatible material comprising a metal, a hard polymer, or an inflatable material.

13. The apparatus of claim 1 wherein the specified tissue is live brain tissue.

14. The apparatus of claim 1 wherein the specified tissue is the brain, wherein the first stylet diameter is 0.050" to 0.100", wherein the second stylet diameter is 0.030" to 0.095", and wherein the stylet comprises one of the group consisting of a metal, a hard polymer, or a composite material.

15. The apparatus of claim 1 wherein the second stylet diameter is configured to be large enough to enable rigidity for penetration and small enough to enable tactile feedback to a user during catheter placement.

16. The apparatus of claim 1 wherein the working area of the catheter has a constant outer diameter.

17. The apparatus of claim 1 wherein the first effective stylet diameter reduces tissue accumulation when the catheter is inserted through the specified volume of tissue, such that after implantation of the catheter, there is less tissue obstructing fluid flow within the catheter compared to without use of the stylet.

18. A medical apparatus for fluid delivery or drainage, the apparatus comprising:
a ventricular catheter having a lumen, a tip, and a plurality of side holes in a working area of the catheter, wherein the lumen has a lumen diameter; and
a stylet comprising:
a lumen blocking portion, wherein the lumen blocking portion has an outer surface which is substantially flush with the lumen in the working area of the catheter, and wherein the lumen blocking portion has a first effective stylet diameter that is 90-99% of the lumen diameter; and
a shaft having a proximal end and a distal end and a second effective stylet diameter, wherein the second effective stylet diameter is less than the first effective stylet diameter, and wherein the lumen blocking portion is positioned at the proximal end of the shaft;
wherein the lumen blocking portion has a length capable of covering at least one side hole in the plurality of side holes when the stylet is fully inserted to the tip of the catheter, wherein the shaft has a rigidity which enables the catheter to penetrate a specified volume of live brain tissue, and wherein the covering of at least one side hole is capable of reducing tissue accumulation in a side hole in the plurality of side holes when the catheter is inserted through the specified volume of live brain tissue.

19. The apparatus of claim 18 wherein the length of the lumen blocking portion covers the entire plurality of side holes when the stylet is fully inserted to the tip of the catheter.

20. The apparatus of claim 18 wherein the length of the lumen blocking portion allows at least a portion of one side hole to remain exposed when the stylet is fully inserted to the tip of the catheter.

21. The apparatus of claim 18 wherein the stylet further comprises a stylet fluid path extending through the length of the lumen blocking portion.

22. The apparatus of claim 18 wherein the side holes have a cross-sectional shape chosen from the group consisting of circular, oval-shaped, curvilinear and diamond-shaped.

23. The apparatus of claim 18 wherein the side holes have edges which are beveled or filleted.

24. The apparatus of claim 18 wherein the second stylet diameter is less than 95% of the first stylet diameter.

25. The apparatus of claim 18 wherein the first stylet diameter is 0.050" to 0.100", wherein the second stylet diameter is 0.030" to 0.095", and wherein the stylet comprises one of the group consisting of a metal, a hard polymer, or a composite material.

26. The apparatus of claim 18 wherein the second stylet diameter is configured to be large enough to enable rigidity for penetration and small enough to enable tactile feedback to a user during catheter placement.

27. The apparatus of claim 18 wherein the working area of the catheter has a constant outer diameter.

* * * * *